United States Patent [19]
Nita et al.

[11] Patent Number: 5,997,497
[45] Date of Patent: *Dec. 7, 1999

[54] ULTRASOUND CATHETER HAVING INTEGRATED DRUG DELIVERY SYSTEM AND METHODS OF USING SAME

[75] Inventors: Henry Nita, Mission Viejo; Timothy Mills, Belvedere Tiburon; Robert Siegel, Venice, all of Calif.

[73] Assignee: Advanced Cardiovascular Systems, Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/878,463

[22] Filed: Jun. 18, 1997

Related U.S. Application Data

[63] Continuation of application No. 08/330,037, Oct. 27, 1994, abandoned, which is a continuation-in-part of application No. 08/094,416, Jul. 19, 1993, Pat. No. 5,397,301, which is a division of application No. 07/640,190, Jan. 11, 1991, Pat. No. 5,304,115.

[51] Int. Cl.$^6$ .................................................. A61B 17/70
[52] U.S. Cl. .............................................. 604/22; 604/523
[58] Field of Search .................... 604/22, 280; 601/2; 607/97; 606/159

[56] References Cited

U.S. PATENT DOCUMENTS

| | | |
|---|---|---|
| 3,809,093 | 5/1974 | Abraham . |
| 4,748,971 | 6/1988 | Borodulin et al. . |
| 4,897,079 | 1/1990 | Zaleski et al. ............................. 604/22 |
| 5,267,954 | 12/1993 | Nita ............................................. 604/22 |
| 5,304,115 | 4/1994 | Pflueger ..................................... 604/22 |
| 5,324,255 | 6/1994 | Passafaro et al. ......................... 604/22 |
| 5,368,557 | 11/1994 | Nita et al. ................................... 604/22 |
| 5,397,301 | 3/1995 | Pflueger et al. ........................... 604/22 |
| 5,498,236 | 3/1996 | Dubrul et al. . |

FOREIGN PATENT DOCUMENTS

| | | |
|---|---|---|
| 0 208 175 | 1/1987 | European Pat. Off. . |
| 0 316 796 | 5/1989 | European Pat. Off. . |
| 2 641 693 | 7/1990 | France . |
| 2 643 272 | 8/1990 | France . |
| 37077921A1 | 9/1987 | Germany . |

*Primary Examiner*—Mark Bockelman
*Attorney, Agent, or Firm*—Fulwider Patton Lee & Utecht, LLP

[57] ABSTRACT

An ultrasound delivery catheter equipped and configured for concurrent delivery of drugs or therapeutic agents. The catheter comprises an elongate pliable catheter body having an ultrasound delivery member or wire extending longitudinally therethrough. A drug/therapeutic agent infusion lumen also extends longitudinally through the body of the catheter and opens distally through one or more outflow apertures at or near the distal end of the catheter body. The drug/therapeutic agent outflow apertures are preferably positioned and configured to cause the drug or therapeutic agent to flow in direction(s) non-parallel to the longitudinal axis of the catheter. The delivery of ultrasound through the catheter, concurrent with infusion of drug or therapeutic agent therethrough, will cause the drug or therapeutic agent to be disseminated or dispersed by the ultrasonic vibration or movement at the distal end of the catheter.

21 Claims, 3 Drawing Sheets

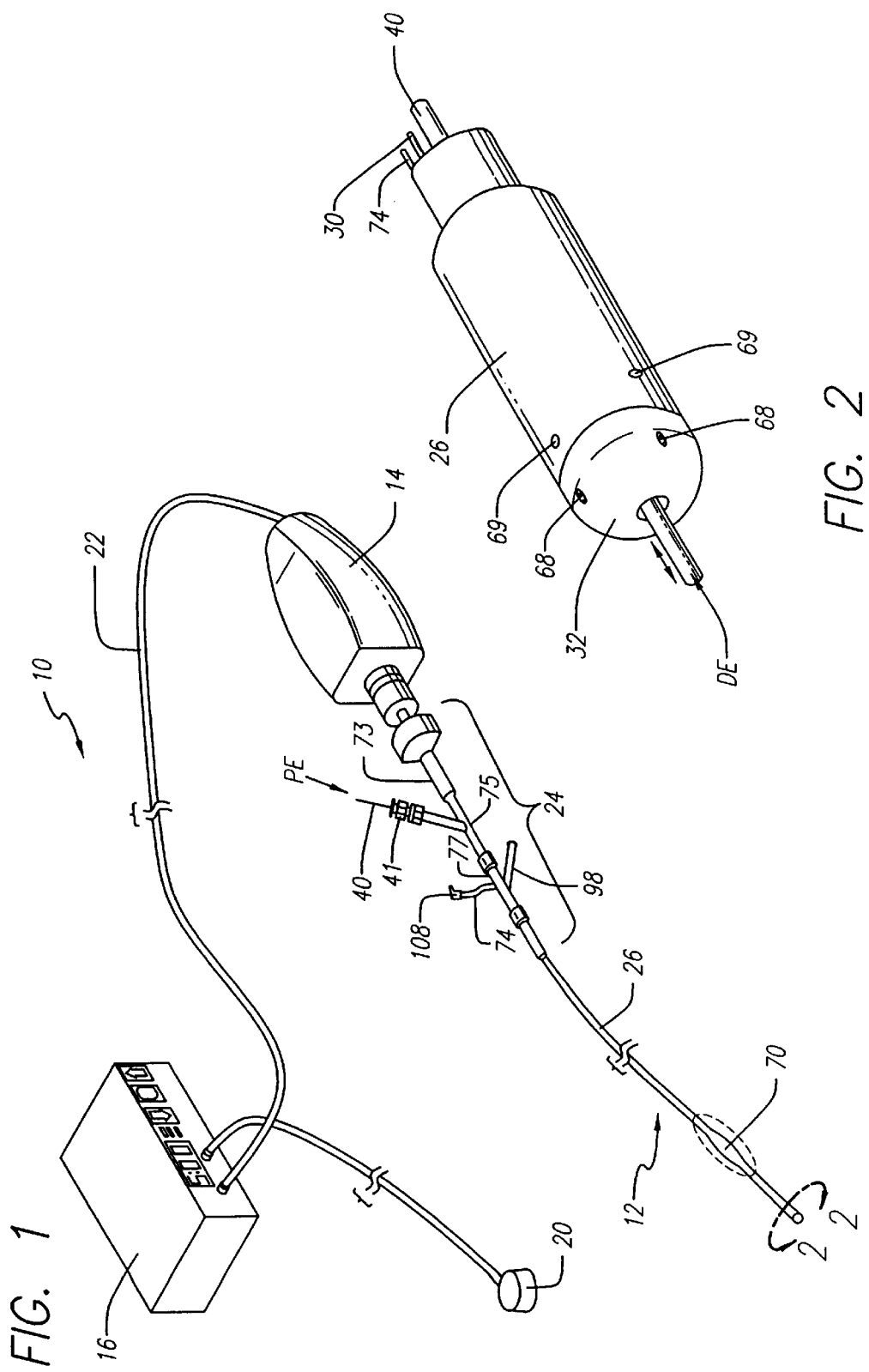

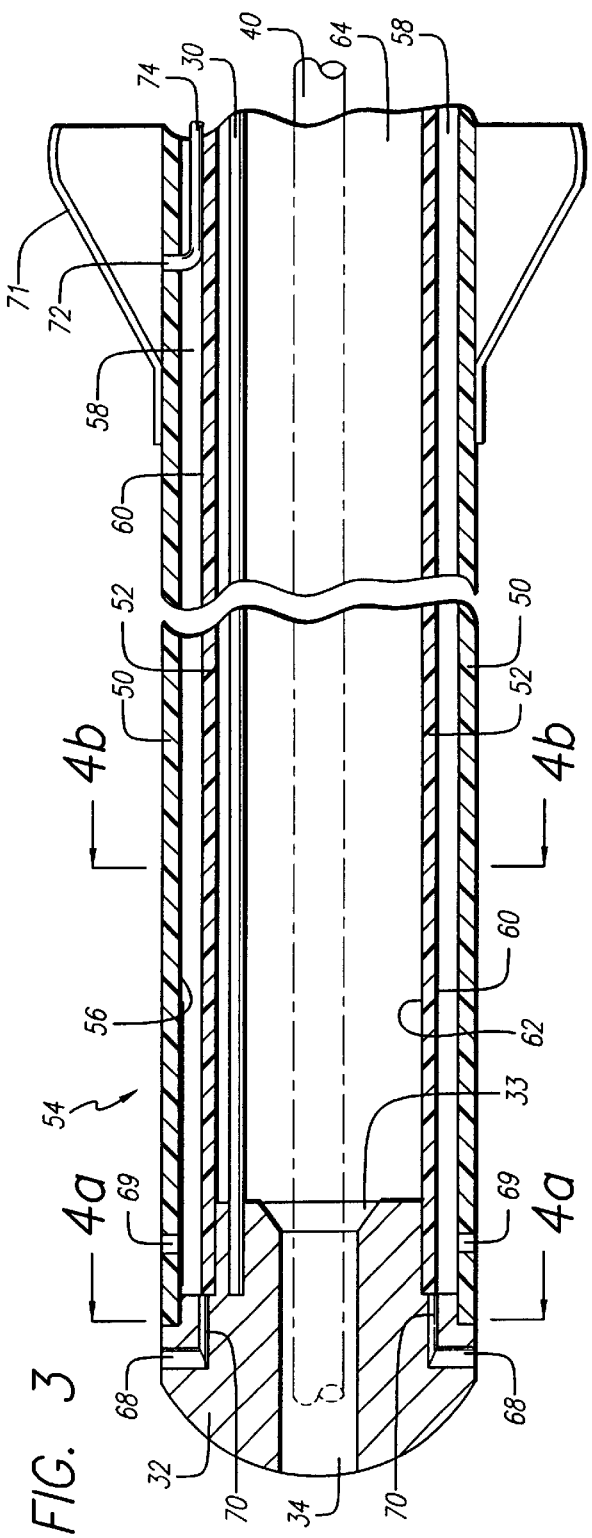
FIG. 3
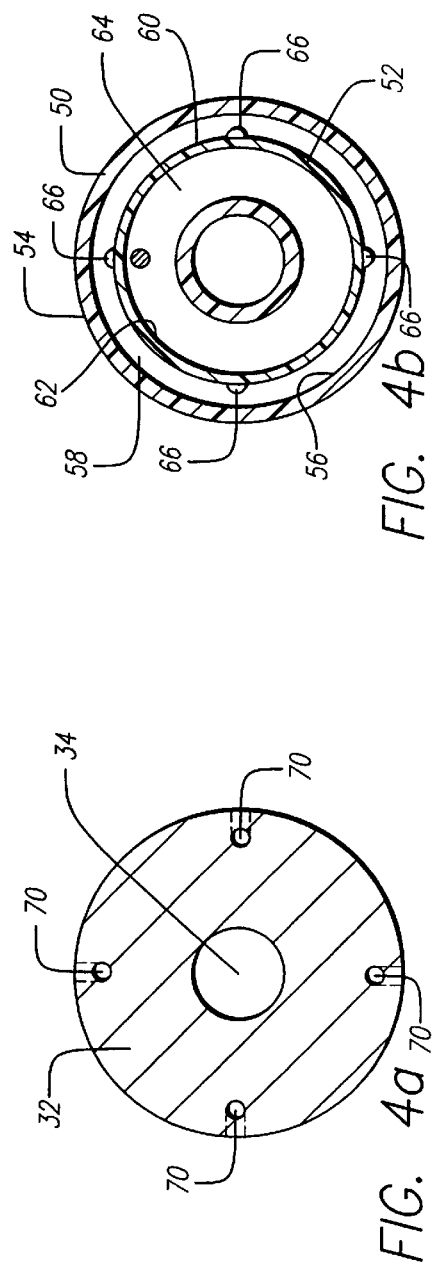
FIG. 4b
FIG. 4a

ULTRASOUND CATHETER HAVING INTEGRATED DRUG DELIVERY SYSTEM AND METHODS OF USING SAME

RELATED APPLICATIONS

This application is a continuation of U.S. patent application Ser. No. 08/330,037 filed Oct. 27, 1994 now abandoned which is a continuation-in-part of U.S. patent application Ser. No. 08/094,416, entitled ULTRASONIC ANGIOPLASTY DEVICE INCORPORATING AN ULTRASOUND TRANSMISSION MEMBER MADE AT LEAST PARTIALLY FROM A SUPERELASTIC METAL ALLOY, filed Jul. 19, 1993 now U.S. Pat. No. 5,397,301, which is a Division of U.S. patent application Ser. No. 07/640,190, entitled ULTRASOUND ANGIOPLASTY DEVICE INCORPORATING IMPROVED ULTRASOUND TRANSMISSION MEMBER AND ABLATION PROBE, filed Jan. 11, 1991 and subsequently issued as U.S. Pat. No. 5,304,115.

FIELD OF THE INVENTION

The present invention relates generally to medical equipment and more particularly to ultrasonic methods and devices which may be utilized to a) cardiovascular obstructions such as athroscloratic plaque or thrombus located in a mammalian blood vessel and b) to deliver an infusion of one or more therapeutic agents or drugs concurrently with ultrasonic energy so that the dissemination, dispersal, distribution, absorption, activity or duration of effected by the ultrasonic energy.

BACKGROUND OF THE INVENTION

A number of ultrasonic devices have heretofore been proposed for use in ablating or removing obstructive material from anatomical structures, such as blood vessels. Examples of devices which purportedly utilize ultrasonic energy, alone or in conjunction with other treatment modalities, to remove obstructions from anatomical structures include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), and 5,100,423 (Fearnot) as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2,438,648 (Pohlman).

Ultrasound transmitting catheters have been utilized to successfully ablate various types of obstructions from blood vessels of humans and animals. Patients who are candidates for ultrasound ablation of vascular obstructions may also be candidates for treatment by various thrombolytic agents (i.e., blood clot dissolving agents) or other therapeutic agents or drugs.

Many types of therapeutic agents or drugs may be delivered by the ultrasonic catheter of the present invention. The types of agents or drugs which may be utilized in cardiovascular applications of the catheter include, but are not necessarily limited to, the following:

i. Thrombolytic Agents

Examples of thrombolytic agents utilized to dissolve thrombotic material include: streptokinase (Streptokinase for Infusion, Astra Pharmaceutical Products, Inc., Westboro, Mass., and Kabikinase®, Kabi Pharmacia, Piscataway, N.J.); urokinase (Abbokinase®, Abbott Laboratories, North Chicago, Ill..); and tissue plasminogen activator (TPA). Such agents are administered intravascularly following myocardial infarction or other cardio vascular events wherein a thrombus is suspected to be in formation or in existence.

ii. Anticoagulant Agents

Examples of anticoagulant agents utilized to prevent the subsequent formation of thrombus or blood clots include heparin (Heparin Sodium Injection, Wyeth-Ayerst Laboratories Philadelphia, Pa.).

In patients who are undergoing ultrasonic angioplasty procedures wherein a vascular obstruction is ablated by way of ultrasonic vibration, the administration of one or more therapeutic agents or drugs may be indicated before, during or after ultrasonic ablative procedure. Thus, it is desirable to design an ultrasonic ablation catheter through which various therapeutic agents or drugs may be delivered.

Additionally, it is desirable to design and devise new catheter devices for concurrently delivering a flow of liquid medicament along with ultrasonic vibration such that the distribution, delivery, absorption and/or efficacy of the medicament may be improved or enhanced by the ultrasonic vibration.

SUMMARY OF THE INVENTION

The present invention provides improved ultrasound delivery catheters which incorporate means for infusing liquid medicaments (e.g., drugs or therapeutic agents) concurrently or in conjunction with the delivery of ultrasonic energy. The delivery of the ultrasonic energy through the catheter concurrently with the infusion of a liquid medicament will aid in rapidly dispersing, disseminating, distributing or atomizing the medicament. Additionally, it is postulated that the infusion of at least some types of liquid medicaments concurrently with the delivery of ultrasonic energy may result in improved or enhanced activity of the medicament due to a) improved absorption or passage of the medicament into the target tissue or matter and/or b) enhanced effectiveness of the medicament upon the target tissue or matter (e.g., thrombus) due to the concomitant action of the ultrasonic energy on the target tissue or matter.

Further in accordance with the invention, there are provided methods for treating various diseases or conditions by administering therapeutic agents or drugs concurrently or in conjunction with the delivery of ultrasonic energy.

Further objects and advantages of the invention will become apparent to those skilled in the art upon reading and understanding of the detailed description set forth herebelow, and consideration of the accompanying drawings.

BRIEF DESCRIPTION OF THE DRAWINGS

FIG. 1 is a perspective view of an ultrasound/therapeutic agent delivery system of the present invention incorporating an ultrasound/therapeutic agent delivery catheter, an ultrasound transducer and an electronic signal generator.

FIG. 2 is an enlarged perspective view of the distal-most portion of the catheter shown in FIG. 1.

FIG. 3 is a longitudinal sectional view of FIG. 2.

FIG. 4a is a cross sectional view through line 4a—4a of FIG. 3.

FIG. 4b is a cross sectional view through line 4b—4b of FIG. 3.

DETAILED DESCRIPTION OF THE PREFERRED EMBODIMENT

Figure 5:
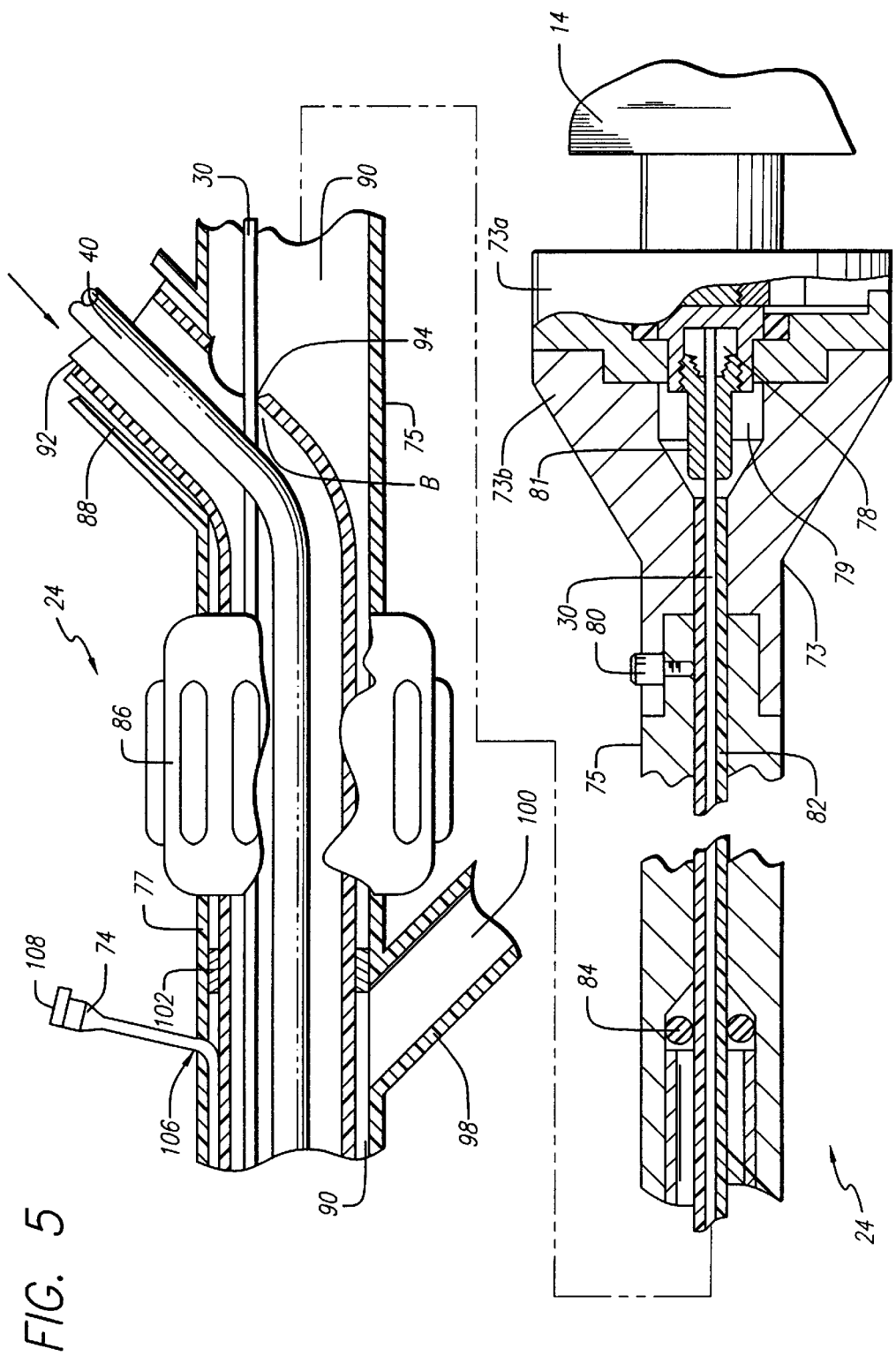
FIG. 5 is a longitudinal sectional view of the proximal connector assembly of the catheter shown in FIG. 1.

The following detailed description and the accompanying drawings are intended to describe and illustrate presently preferred embodiments of the invention only, and are not intended to limit the scope of the invention in any way. Indeed, the particular embodiments described herebelow are not the only embodiments in which the invention may be constructed and utilized.

FIG. 1 shows an ultrasound ablation/drug delivery system 10 of the present invention. The system 10 generally comprises an elongate ultrasound ablation/drug delivery catheter 12, an ultrasound transducer 14 and an electrical signal generator 16.

The signal generator 16 comprises a device operable to generate various wave-form electrical signals, such as the device available as Model UAG1110, Baxter Healthcare Corporation, Cardiovascular Group, Interventional Cardiology Division, Irvine, Calif. The preferred signal generator 16 incorporates a foot pedal on/off switch 20 for hand-free actuation/deactuation of the signal generator 16. The signal generator 16 is connected to ultrasound transducer 14 by way of cable 22. The ultrasound transducer 14 is operative to convert an electrical signal received from the signal generator 16, to ultrasonic energy. One example of an ultrasound transducer 14 usable in the system 10 is that commercially available as model UAT-1000, Baxter Healthcare Corporation, Cardiovascular Group, Interventional Cardiology Division, Irvine, Calif.

The ultrasound catheter 12 of the present invention comprises an elongate flexible catheter body 26 having an elongate ultrasound transmission member or wire 30 which extends longitudinally therethrough. A proximal connector assembly 24 is positioned on the proximal end of the catheter body 26. As shown in detail in FIG. 5, and described more fully herebelow, the proximal connector assembly 24 includes a sonic connector apparatus 79 which facilitates connection of the proximal end of the ultrasound transmission member 30 to the ultrasound transducer 14 such that ultrasonic energy from the transducer 14 may be transmitted, in the distal direction, through the ultrasound transmission member 30 to the distal end of the catheter 12.

The ultrasound transmission member 30 of the present invention may be formed of any suitable material capable of carrying ultrasonic energy from the proximal end of the catheter 12 to the distal end thereof. In particular, the presently preferred embodiment of the ultrasound transmission member 30 is formed of nickel-titanium alloy which exhibits superelastic properties within the temperature range under which the device is operated.

In particular, one presently preferred superelastic metal alloy of which the ultrasound transmission member 30 may be formed is nickel-titanium alloy consisting of 50.8 atomic percent nickel/balance titanium and is commercially available as Tinel® BB from Raychem Corporation, Menlo Park, Calif.

The physical properties of the preferred 50.8 atomic percent nickel NiTi alloy are as follows:

| Properties of NiTi Alloy Having 50.8 At. % Nickel/Balance Titanium | | |
|---|---|---|
| Property * | Units | Value |
| Superelastic Temperature Range | ° C. | 20 to 80 |
| Loading Plateau Stress (at 20° C.) | Mpa | 480 |
| Unloading Plateau Stress | Mpa | 135 |
| Permanent Set (at 20° C. after 8% strain) | % | 0.2 |
| Ultimate Tensile Strength (at 20° C.) | Mpa | 1150 |
|  | Ksi | 170 |
| Elongation at Failure | % | 10 |
| Melting Point | ° C. | 1350 |
| Density | g/cm | 6.5 |
|  | lbs/cu.Inch | 0.235 |

* Typical Values for Cold Worked and Shape Set Condition

Examples of superelastic metal alloys which are useable to form the ultrasound transmission member 22 of the present invention is described in detail in the U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are superelastic within the temperature range at which the ultrasound transmission member 22 of the present invention operate, any and all of which superelastic metal alloys may be useable to form the superelastic ultrasound transmission member 22.

In the preferred embodiment, the ultrasound transmission member 30 may be specifically configured and constructed to provide desirable flexibility or bendability near the distal end of the catheter, while at the same time minimizing the likelihood of breakage or fracture of the ultrasound transmission member 24 during use. Bendability or pliability of the distal portion of the catheter is particularly desirable in coronary or cerebrovascular applications wherein the distal portion of the catheter is required to pass into small tortuous coronary or cerebral blood vessels.

In the particular embodiment shown, the catheter body 26 is constructed of an outer tube 50 and an inner tube 52. The outer tube 50 has an outer surface 54 and an inner surface 56. The outer surface 54 of the outer tube 50 forms the outer surface of the catheter body 26, having an outer diameter $D_1$. The inner surface 56 of the outer tube 50 forms the inner or luminal surface of the outer tube lumen 58, having an inner diameter $D_2$.

Inner tube 52 has an outer surface 60 and an inner surface 62. The outer surface 60 of inner tube 52 has an outer diameter $D_3$. The inner surface 62 of the inner tube 52 forms the inner or luminal surface of the inner tube lumen 64, and has an inner diameter $D_4$.

As shown, the inner tube 50 is coaxially positioned within the lumen 58 of the outer tube 50. The outer diameter $D_3$ of the inner tube 52 is smaller than the inner diameter $D_2$ of the outer tube 50, so as to provide a gap or space between the luminal surface 56 of the outer tube 50 and the outer surface 60 of the inner tube 52, through which a liquid medicament may be infused.

The distal tip member 32 of the catheter 12 has a plurality of hollow medicament passageways 70 bored or otherwise formed therein and opening through medicament outflow apertures 68 formed in the outer surface of the distal tip member 32, to permit a liquid medicament being infused through the space between the inner tube 52 and the outer tube 50 to pass through the distal tip member 32 and out of the outflow apertures 68 formed therein.

Also, additional medicament outlet apertures 69 may be formed in the wall of the outer tube 50, near the distal end thereof, such that some of the medicament being infused through the space between the inner tube 52 and outer tube 50 will flow outwardly through such apertures 69. In the embodiment shown in FIGS. 2–3, the additional medicament outlet apertures 69 are paired with, and located in spaced relation to the outflow apertures 68 formed in the distal tip members 32. It will be appreciated, however, that various other arrangements and positionings of the respective medicament outlet apertures 68, 69 may be utilized without departing from the intended purpose and function of the present invention. The size and numerousity of the medicament outlet apertures 68, 69 may vary depending on the specific intended function of the catheter 12, the volume or viscosity of the medicament intended to be infused, and/or the relative size of the therapeutic area to which the medicament is to be applied.

A guide wire passage bore 34 extends longitudinally through the distal tip member 32 and is provided with a chamfered or frustoconical proximal region 33 to facilitate distally directed entry of the distal tip of an advancing guidewire 40 into the proximal opening of the guide wire passage bore 34.

An optional annular occlusion balloon 71 or inflatable collar may be mounted or formed on the outer surface 54 of the catheter body 26 at a location proximal to the medicament outflow apertures 68, 69 to temporarily occlude blood flow through the blood vessel in which the catheter 12 is positioned. In the embodiment shown the balloon 71 comprises a cylindrical elastic membrane mounted on the outer surface 54 of the outer tube 50. A balloon inflation aperture 72 is formed in the side wall of the outer tube 50, at a location beneath the balloon 71. A small balloon inflation tube extends through the outer tube lumen 58, outboard of the outer surface 60 of inner tube 52, and is connected to the balloon inflation aperture 72 such that the balloon 71 may be inflated by injecting balloon inflation fluid through balloon inflation tube 74 and deflated by withdrawing balloon inflation fluid through tube 74.

The proximal connector assembly 24, as shown in FIGS. 1 and 5, is mounted on the proximal end of the catheter body 26 and operates to connect the catheter 12 to an a) ultrasound transducer, b) a source of coolant fluid, c) a source of medicament for infusion and d) a source of balloon inflating fluid for inflating the annular occlusion balloon 71. As shown, the preferred proximal connector assembly 24 generally comprises first 73, second 75 and third 77 rigid body portions.

The first body portion 73 of the proximal connector assembly 24 is made up of two separate mated parts 73a, 73b, and forms the proximal-most end of the connector assembly 24. A receiving depression (not shown) is formed in the proximal face of the first body portion 73, to receive therein to facilitate connection of the transducer horn to the proximal end of the ultrasound transmission member 40. The transmission of ultrasonic vibration from the transducer 14 into the ultrasound transmission member 40 is facilitated by a sonic connector apparatus 79 which is assembled and retained within the first body portion 73 of the proximal connector assembly 24.

The sonic connector apparatus 79 comprises a compressible gripping ferrule 78 having a small central aperture formed therethrough, through which the ultrasound transmission member 40 passes, as shown. A frontal compression member 81 is threaded onto, and exerts inward pressure upon, the gripping ferrule 78 gripping ferrule 78 such that it frictionally engages the outer surface of the ultrasound transmission member 40 extending therethrough. This holds the ultrasound transmission member 40 in its desired longitudinal position. The proximal tip of the ultrasound transmission member 40 extends into the receiving depression (not shown) formed in the proximal face of the first portion 73 and is provided with a threaded sleeve (not shown) to threadably couple with the distal horn of an ultrasound transducer 14. By such arrangement, ultrasonic energy may pass directly from the horn of the ultrasound transducer 14 into the ultrasound transmission member 40, and will be carried thereby to the distal end of the catheter 12.

The second body portion 75 of the proximal connector assembly 24 is connected to the first portion 73, and secured thereto by way of set screw 80. A hollow inner bore 90 extends longitudinally through the second and third body portions 75, 77, as shown. A lateral damping tube 82 is axially positioned around the portion of the ultrasound transmission member 30 which extends in the proximal direction from bore 90, into the first body portion 73 of the connector assembly 24. Such damping tube 82 is maintained in its substantially centered position within bore 90 by O-ring 84. Such damping tube 82 serves to limit the amount of side to side or lateral movement that the ultrasound transmission member 40 may undergo in the region immediately proximal to the sonic connector apparatus 79. The provision of such damping tube 82 serves to minimize the likelihood of breakage or fracture of the ultrasound transmission member 40 in the region immediately adjacent the point at which the ultrasound transmission member 40 is coupled to the ultrasound transducer 14.

The third body portion 77 of the proximal connector assembly 24 is coupled to the proximal end of the catheter body 26 such that bore 90 is in fluid communication with the outer tube lumen 58. A guide wire/coolant infusion side arm 88 extends laterally from the third portion 74 of the connector assembly 24, and forms an inlet/outlet into the hollow inner bore 90 thereof. A curved guide wire diverter tube 92 is positioned within guide wire/coolant infusion side arm 88 and extends, in curved configuration, into the inner bore 90 of the proximal connector assembly 24. The guide wire diverter tube 92 continues in the distal direction and is connected to the proximal end of the inner tube 52 of the catheter body 26 such that the lumen of the guidewire diverter tube 92 is continuous with the lumen of the inner tube 52 of the catheter. An aperture 94 is formed in the proximal side of the bend B formed in the guide wire diverter tube 92 and the ultrasound transmission member 40 passes directly into the lumen of the guide wire diverter tube 92. The ultrasound transmission member 40 extends distally through the lumen of the diverter type 92 and through the lumen 64 of the inner tube 52 of the catheter body 26, as shown. The angular bend B of the guidewire diverter tube 92 is configured to divert the advancing end of a guidewire 40 out of the guide wire/coolant infusion side arm 88. By such configuration, the proximal end of a guide wire 40 may be inserted into the guidewire passage bore 34 and advanced proximally through the catheter body, and through the lumen 93 of the guide wire diverter tube 92 to a point where the proximal end of the guide wire will contact against the obtuse bend B, being thereby directed outwardly through the guide wire/coolant infusion sidearm 88. Thus, the guide wire diverter tube 92 operates to guide or deflect the advancing proximal end of a guide wire 40 out of the guidewire/coolant infusion sidearm 88, rather than allowing the guidewire to continue in the straight proximal direction through the bore 90 and into the first portion 73 of the proximal connector assembly 24.

A guide wire gripping apparatus 41 such as that commercially available as product Nos. 1905017A and 1905014A from Medical Disposables International, West Conshocken, Pa., may be positioned on the guide wire side arm 88 to grip and hold the guide wire 40, thereby preventing unwanted back and forth movement of the guide wire 40. When it is desired to advance or retract the guide wire 40, the guide wire gripping apparatus 41 may be loosened and the guide wire may be manipulated or removed as desired.

After the guide wire 40 has performed its required function, the guide wire gripping apparatus 41 may be loosened and the guide wire 40 may be extracted and removed. Thereafter, the guide wire gripping apparatus 41 may be removed from the guide wire/coolant infusion side arm 88. A coolant infusion line may then be connected to guide wire/coolant infusion side arm 88 to provide a flow of coolant solution (e.g., sterile 0.9 percent NaCl solution) through the lumen of the guide wire diverter tube 92, through the inner tube lumen 64 of catheter 12, and out of the open guide wire passage bore 34 in the distal tip member 32 of the catheter 12. Also, some coolant fluid will pass through the aperture 94 formed in the guide wire diverter tube 92 so as to fill the inner bore 90 of the proximal connector assembly 24, in the region proximal to the point where the ultrasound transmission member 30 enters the guide wire diverter tube 92. (FIG. 5) Thus, the infusion of coolant fluid into the guide wire/coolant infusion side arm 88 will bath the ultra sound transmission member 30 and prevent overheating and potential thermal damage to the ultrasound transmission member 30 during operation.

The third portion 77 of the connector assembly 24 incorporates a forward extension attached by nut 86 and having a medicament infusion side arm 98 which extends laterally therefrom. The hollow bore 100 of the medicament infusion side arm 98 provides an opening into the inner bore 90 of the connector assembly 24, outboard of the outer surface of the guide wire diverter tube 92. As such, a medicament drug solution, such as a liquid therapeutic agent, or other liquid may be infused through medicament infusion side arm 98, through the inner bore 90 of the connector assembly, through the outer tube lumen 58 of the catheter body 26 (outboard of the inner tube 52 disposed therewithin), and out of the medicament outflow apertures 68, 69 at the distal end of the catheter 12. An annular seal member 102 is mounted around the outer surface of the guide wire diverter tube 92, at a location immediately proximal to the infusion side arm 98, so as to form a seal between the outer surface of the guide wire diverter tube 92, and the inner surface of the bore 90 of the proximal connector assembly 24, thereby preventing the infused medicament or other liquid through medicament infusion side arm 98 from backflowing in the proximal direction through the connector assembly 24. Thus, any drug solution therapeutic agent or other fluid infused through infusion side arm 98 will be caused to flow only in the distal direction, through the outer tube lumen 58 of the catheter 12 and out of medicament outflow apertures 68, 69.

Also, a balloon inflation tube escape aperture 106 is formed in the side wall of the 77 of the connector assembly 24. The proximal end of the balloon inflation tube 74 is exteriorized through the aperture 106 and a fluid tight seal is formed therearound to prevent fluid from leaking from the bore 90 outwardly through aperture 106. A Leur connector 108 is mounted on the proximal end of the balloon inflation tube 74 to facilitate attachment of a stop cock (not shown) balloon inflation and syringe (not shown) thereto.

OPERATION OF THE PREFERRED EMBODIMENT

In accordance with standard clinical procedures, a guide wire 40 may be initially percutaneously inserted, and advanced through the vasculature to a point where the distal end DE of the guide wire 40 is positioned near or adjacent the intravascular obstruction to be ablated. Thereafter, the exteriorized proximal end PE of the guide wire may be directed inwardly through the guide wire passage bore 34 which extends through the distal tip member 32 of the catheter 12, and the catheter 12 may then be advanced in the distal direction, over the guide wire 30. As the inner tube lumen 64 advances distally over the preinserted guidewire 40, the proximal end PE of the guidewire 40 it will enter the guidewire diverter tube 92 positioned within the proximal connector assembly 24. As the proximal end PE of the guide wire 40 reaches the obtuse bend B of the guide wire diverter tube 92, the proximal end PE of the guide wire 40 will be thereby deflected in the lateral direction, so as to pass outwardly through the guide wire/coolant infusion side arm 88. When the catheter 12 has been advanced to its desired operative position (i.e., when the distal tip member 32 of the catheter 12 is positioned adjacent or in contact with the thrombus or other obstruction to be ablated) the guide wire gripping apparatus 41 may be tightened to hold the catheter 12 in a fixed longitudinal position relative to the guide wire 40. Alternatively, the guide wire 40 may be fully extracted and removed, through the guide wire side arm 88.

After the catheter 12 has been advanced to its desired operative position, the ultrasound transducer 14 is connected or coupled, by way of the sonic connector apparatus 77, to the proximal end of the ultrasound transmission member 30 such that ultrasonic vibration may be transmitted from the horn of the ultrasound transducer 14, through the ultrasound transmission member 30, and to the distal end of the catheter 12.

After the guide wire 40 has been extracted and removed, the guide wire gripping apparatus 41 may be detached and removed from side arm 88 and an infusion tube may be connected to side arm 88 to infuse a flow of coolant fluid, such as sterile 0.9 percent saline solution, through guide wire/coolant infusion side arm 88, through the inner tube lumen 64 of the catheter 12, and out of the guide wire passage bore 34 of the distal tip member 32. Such flow of infusion fluid will serve to cool the ultrasound transmission member 40 during operation thereof.

As the coolant fluid is being infused, the signal generator 16 is actuated by depression of on/off foot pedal 20, thereby sending an electrical signal from the signal generator 16 to ultrasound transducer 14. The ultrasound transducer 14 then converts the received electrical signal into ultrasonic energy and such ultrasonic energy is then transmitted through the ultrasound transmission member 40 to the distal tip member 32 of the catheter 12. The vibrating distal tip member 32, being in abutment with and attached to the distal end of the catheter body, will cause the adjacent distal portion of the catheter body 26 to vibrate as well. As the distal portion of the catheter 12 vibrates, the operator may move the catheter 12 back and forth to cause the distal end of the catheter to traverse the region of the thrombus or occlusion to be ablated such that the ultrasonic vibration of the distal tip member 32 and adjacent distal portion of the catheter body 26 will cause ultrasonic ablation of the thrombus or other obstructive matter.

Concurrent with the delivery of ultrasound to the distal tip member 32 and adjacent distal portion of the catheter body 26, a flow of liquid medicament may be infused through medicament infusion side arm 98, through the outer tube lumen 58 (outboard of the outer surface 60 of the inner tube 52) through drug infusion passageway 70 and out of the medicament outlet apertures 68, 69 formed at spaced locations around the outer surface of the distal catheter body 26 and distal tip member 32. The concomitant delivery of ultrasound causes the distal member 32 and the adjacent distal portion of the catheter body 26 to vibrate in a manner which causes the medicament flowing out of apertures 68 and 69 to become thoroughly disseminated, dispersed or atomized. Additionally, the effect of the ultrasonic vibration on the adjacent vascular tissue and/or matter (e.g., thrombus) to be ablated may enhance the action of the medicament on the adjacent vascular tissue and/or matter to be ablated.

After the ablation procedure has been completed, and the desired dose of medicament has been delivered, the catheter 12 may be extracted and removed from the body.

The concurrent delivery of the medicament with ultrasonic vibration may improve the dissemination and delivery of the medicament from the catheter tip due to the physical dispersing or atomizing effect of the vibration of the catheter 12. Also, for at least some drugs or therapeutic agents, the local absorption and/or effectiveness of the drug or therapeutic agent may be improved or enhanced by a physiological effect of the ultrasound acting on the adjacent tissue or matter being acted upon by the drug or therapeutic agent. For example, physiological effects of ultrasound on vascular tissue have been described in the following publications: Fischell, T. A., Derby, G., Tse, T. M. and Stadius, M. L.; Coronary Artery Vasoconstriction Routinely Occurs After Percutaneous Transluminal Coronary Angioplasty: A Quantitative Arteriographic Analysis; Circulation; Vol 78; 1323–1334 (1988); Chokahi, S. K., et al., ULTRASONIC ENERGY PRODUCES ENDOTHELIUM-DEPENDENT VASOMOTOR RELAXATION IN VITRO, Abstracts of the 62nd Scientific Sessions of the American Heart Association (1989).

EXAMPLE

The following are illustrative examples of clinical situations in which the above-described ultrasound delivery/drug infusion catheter may be utilized.

Example I
Post Infarct Ablation of a Coronary Obstruction with Concomitant Delivery of a Thrombolytic Agent Following the diagnosis of an acute myocardial infarction in a human patient, it is determined radiographically that the left anterior descending coronary artery is significantly occluded and that blood flow to the infarcted myocardium is thereby impaired.

A coronary guide catheter is inserted, percutaneously, into the patient's femoral artery and such guide catheter is advanced to a location where the distal end of the guide catheter is in the left coronary ostium. A guide wire 40 is advanced through the lumen of the guide catheter to a location where the distal end DE of the guidewire 40 is immediately adjacent or actually passed through the obstruction within the left anterior descending coronary artery. With such positioning of the guide wire 40 may be confirmed by fluoroscopic means.

A catheter 12 of the present invention, as shown in FIGS. 1–5, is advanced over the prepositioned guide wire 40 by inserting the exteriorized proximal end of the guide wire into the guide wire passage bore 34 formed in the distal tip 32 of the catheter 12. The catheter 12 is advanced over the guide wire 40, such that the proximal end of the guide wire 40 will emerge out of guide wire/coolant infusion side arm 88. When the catheter 12 has been advanced to a point where the distal end of the catheter 12 is immediately adjacent the coronary obstruction to be ablated, the guide wire 40 may be extracted through guide wire/coolant infusion side arm 88 and removed.

Thereafter, a bag or other container of sterile 0.9 percent NaCl solution may be connected, by way of a standard solution administration tube, to the guide wire/coolant infusion side arm 88 and a slow flow of saline solution may be pumped or otherwise infused through sidearm 88, through the inner tube lumen 64, and out of the guide wire passage bore 34 of the catheter 12. An intravenous infusion pump or intravenous bag compression apparatus may be utilized to provide such flow of coolant fluid through the catheter.

The proximal connector assembly 24 of the catheter 12 is connected to the ultrasound transducer 14, and the ultrasound transducer 14 is correspondingly connected to the signal generator 16 so that, when desired, ultrasonic energy may be passed through the catheter 12.

A 1 cc tuberculin syringe filled with room air or carbon dioxide ($CO_2$) is attached to the Luer connector 108 on the proximal end of the balloon inflation tube 74 and may be utilized to inflate and deflate the occlusion balloon 71, as required.

An intravenous infusion bag or other container containing a prepared liquid solution of Tissue Plasminogen Activator (TPA) is connected, by way of standard intravenous infusion tubing, to medicament infusion side arm 98. An intravenous infusion pump is coupled to the infusion tubing to permit control over the rate at which the TPA solution is infused through the catheter 12.

When it is desired to commence the ablative procedure, the flow of coolant infusion through guide wire/coolant infusion side arm 88 is maintained at an appropriate slow flow rate while the signal generator 16 is periodically actuated/deactuated by compression/non-compression of on/off foot pedal 20. When actuated, the electrical signals from the signal generator 16 will pass through cable 22 to ultrasound transducer 14. Ultrasound transducer 14 converts the electrical signals into ultrasonic energy and the ultrasonic energy is passed through the ultrasound transmission member 30 of the catheter 12 to the distal end of the catheter 12.

The catheter 12 may be manipulated back and forth by the operator to ablate the entire obstructive lesion, thereby restoring patency to the occluded coronary artery.

Before, during or after the ultrasonic ablative procedure, a prescribed amount of the TPA solution may be infused through medicament infusion side arm 98, by actuation and adjustment of the intravenous infusion pump or other infusion system being utilized. Such will cause the TPA solution to flow, at a prescribed rate, out of the medicament outlet apertures 68, 69 the catheter 12. Such passage of the TPA solution out of the medicament outlet aperture 68, 69 concurrently with the ultrasonic vibration of the distal tip 32 and distal portion of the catheter body 26 will result in vibratory dispersion or atomization of the TPA solution as it passes out of the medicament outlet aperture 68.

During time periods when the TPA solution is being infused through the catheter 12, it may be desirable to inflate the occlusion balloon 71 to block bloodflow through the artery while the TPA solution is being infused. It may be desirable to periodically deflate the balloon 71 to restore perfusion through the left anterior descending coronary artery or alternatively, to deliver an oxygenated perfusate as the coolant fluid being infused through the catheter 12 oxygenated perfusate will pass out of the guidewire bore to the myocardium even when the balloon 70 is inflated.

After the ultrasonic ablation procedure has been completed, and after the desired dose of TPA has been delivered through the catheter 12, the infusion of TPA through medicament infusion side arm 98 will be ceased and the signal generator 16 will be deactuated.

The syringe mounted on the proximal end of the balloon inflation tube 74 will be checked to make certain that the balloon 70 is fully deflated, and the catheter 12 will be extracted from the coronary artery, into the guide catheter.

Thereafter, the guide catheter, with the ultrasound delivery/medicament infusion catheter 12 positioned therein, may be retracted and removed from the body.

By the above-described procedure, the ultrasound delivery/medicament infusion system 10 of the present invention has been used to remove an obstruction from the coronary artery of a post-myocardial-infarction patient, and to concomitantly deliver a desired dose of TPA to the affected myocardium so as to minimize the severity of myocardial damage which may result from the infarct, in accordance with standard thrombolytic post-infarction treatment protocols.

Example II
Treatment of a Peripheral Vascular Obstruction with Concomitant Delivery of VasoDilating Drugs In this example, the ultrasound delivery/medicament infusion system 10 of the present invention is utilized to ablate a thrombotic obstruction in a leg artery of a human patient, and to deliver a vasodilating medication to prevent and/or treat vasoconstriction which may occur prior to, during or after the ultrasonic ablation procedure.

A guidewire 40 is initially inserted percutaneously and advanced to a location within the vasculature, adjacent the obstruction to be treated. Thereafter, the catheter 12 is advanced over the guidewire by inserting the proximal end of the guidewire into the guidewire passage bore 34 and advancing the catheter in the distal direction such that the proximal end of the guide wire enters the guide wire diverter tube 92 of the proximal connector assembly 24 of the catheter, and is diverted thereby out of guide wire/coolant infusion side arm 88.

When the distal end of the catheter 12 has reached its desired operative position adjacent the obstruction to be treated, the guide wire 40 may be extracted and removed and a coolant solution (e.g., sterile 0.9 percent NaCl solution) may be infused through guide wire/coolant infusion side arm 88 in accordance with standard clinical solution administration procedure. The flow rate of coolant solution through the catheter 12 may be adjusted such that a constant slow infusion is maintained.

An intravenous solution bag containing a prepared solution of hydralazine (Apresolone® Parenteral, CIBA Pharmaceutical Company, Summit, N.J.), is connected to medicament infusion side arm 98 by standard solution administration tubing and an intravenous pump is attached to the tubing to control the rate at which the hydralazine solution is infused through the catheter 12.

A 1 cc tuberculin syringe may be inserted into the leur connector 108 on the proximal end of the balloon inflation tube 74 to permit periodic inflation/deflation of the occlusion balloon 70.

The proximal connector assembly 24 of the catheter 12 is connected to the ultrasound transducer 14 and the signal generator 16 is periodically actuated to deliver a preset electrical signal through cable 22 to transducer 14. Transducer 14 converts the received electrical signal to ultrasonic vibration and such ultrasonic vibration is passed through the ultrasound transmission member 30 to the distal end of the catheter 12.

The catheter 12 may be manually manipulated back and forth such that the ultrasonic vibration of the distal tip member 32 and distal portion of the catheter body 26 will effect ultrasonic ablation of the thrombotic obstruction within the leg artery of the human patient.

Concurrently with the delivery of ultrasonic vibration through the catheter 12, the hydralazine solution may be infused, at a prescribed rate, through medicament infusion side arm 98, through catheter 12, and out of medicament outflow apertures 68 and 69. The infusion of the hydralazine solution simultaneously with the delivery of ultrasonic vibration will result in the hydralazine solution flowing out of medicament outflow apertures 68, 69 becoming atomized or dispersed due to the vibratory movement of the distal tip member 32 and distal catheter body 26. Also, because ultrasonic energy has been demonstrated to relax vascular smooth muscle, the concomitant delivery of the ultrasonic energy through the catheter will cause adjacent the blood vessel to remain in a relaxed state, thereby allowing the hydralazine to act on the blood vessel in the absence of significant vasoconstriction. The duration of pharmacologic effect of the hydralazine administration may help to prevent post-ablation vasoconstriction of artery after the catheter 12 has been withdrawn and removed.

During the period of time when the hydralazine solution is being infused through the catheter 12, it may be desirable to utilize a syringe mounted on the proximal end of the balloon inflation tube 74 to inflate the occlusion balloon 71, thereby blocking blood flow through the artery and preventing the hydralazine solution from back flowing beyond the occlusion balloon 71.

After the ultrasonic ablation procedure has been completed and the desired dose of hydralazine has been delivered to the blood vessel, the syringe on the proximal end of the balloon inflation tube 74 will be checked to make certain that the balloon 71 is fully deflated and the catheter 12 may be withdrawn and removed.

Although the invention has been described hereabove with respect to certain presently preferred embodiments, it will be appreciated that various changes, modifications, deletions and alterations may be made to such above-described embodiments without departing from the spirit and scope of the invention. Accordingly, it is intended that all such changes, modifications, additions and deletions be incorporated into the scope of the following claims.

What is claimed is:

1. An ultrasound delivery/medicament infusion catheter for delivering ultrasonic energy to a treatment location within a mammalian body concomitantly with an infusion of medicament, said catheter comprising:

an elongate flexible catheter body having a longitudinal axis, a proximal end, a distal end, an outer surface, and at least one hollow lumen extending longitudinally therethrough;

an ultrasound distal tip member disposed at the distal end of the catheter body;

an ultrasound transmission member extending longitudinally through said catheter body and being connected at the distal end thereof to the distal tip member, said ultrasound transmission member being coupleable to an ultrasound source such that ultrasonic vibration from said ultrasound source may be transmitted through said ultrasound transmission member to the ultrasonic distal tip member at the distal end of said catheter;

a medicament inlet formed near the proximal end of said catheter body for infusing a liquid medicament through a hollow lumen of said catheter; and at least one medicament outlet aperture formed in the distal tip member and oriented radially outward in relation to the longitudinal axis of the catheter body and in fluid communication with the medicament inlet through the hollow lumen to permit medicament to flow out of said catheter generally along the radial direction;

whereby liquid medicament may be infused through said catheter, and out of said medicament outlet aperture(s), concurrently with the delivery of ultrasonic energy to the distal end of the catheter.

2. The catheter of claim 1 wherein the distal end of said ultrasound transmission member is frictionally engaged to said distal tip member.

3. The catheter of claim 1 wherein said catheter lumen has an open distal end and the distal tip member is plug-like in shape and is inserted into the distal end of said lumen and affixed to said catheter body, and further wherein said ultrasound transmission member extends through said lumen of said catheter body and is anchored to said distal tip member.

4. The catheter of claim 1 further comprising at least one medicament outlet aperture formed in the outer surface of said catheter body, adjacent the distal end thereof and oriented radially outward in relation to the longitudinal axis of the catheter body.

5. The catheter of claim 1 wherein said at least one medicament outlet aperture comprises a plurality of medicament outlet apertures formed at spaced apart locations about the outer surface of said distal tip member.

6. The catheter of claim 5 further comprises:

a plurality of medicament outlet apertures formed at spaced apart locations about the outer surface of said catheter body, adjacent said distal tip member.

7. The catheter of claim 5 wherein the plurality of medicament outlet apertures are oriented so that they face radially outward in relation to the longitudinal axis of the catheter body.

8. The catheter of claim 1 wherein said elongate flexible catheter body comprises:

an outer tube having a proximal end a distal end an a hollow lumen extending longitudinally therethrough; and an inner tube having a proximal end, a distal end and a hollow lumen extending longitudinally therethrough;

said inner tube being longitudinally disposed within the lumen of said outer tube.

9. The catheter of claim 8 wherein the distal tip member is affixed to the distal ends of said inner and outer tubes.

10. The catheter of claim 9 wherein:

said outer tube has an inner diameter and an outer diameter; and, said inner tube has an inner diameter and an outer diameter;

the outer diameter of said inner tube being smaller than the inner diameter of said outer tube such that a medicament infusion space exists between the outer surface of said inner tube and the inner surface of said outer tube; and wherein said medicament inlet port and said medicament outlet aperture(s) are in fluid communication with said space to facilitate infusion of liquid medicament therethrough.

11. The catheter of claim 10 wherein said medicament outlet aperture(s) comprises:

a plurality of apertures formed in said distal tip member around the periphery thereof and oriented radially outward such that medicament flowing through said space will pass out of said medicament outlet apertures.

12. The catheter of claim 1 further comprising:

a hollow guidewire passage bore extending longitudinally through the distal end of said catheter.

13. A system for delivering ultrasonic energy along with a flow of liquid medicament to a treatment location within a mammalian body, said system comprising:

the catheter of claim 1 in combination with;

an electrical signal generator for generating an electrical wave form signal;

an ultrasound transducer connected to said signal generator for converting said electrical signal to ultrasonic energy; and said ultrasound transducer being coupled to the proximal end of the ultrasound transmission member of said catheter.

14. The catheter of claim 12 wherein said guidewire passage bore is located separately from the lumen so that it is not in fluid communication with the lumen;

whereby cooling fluid may be applied through the guidewire passage bore while medicament is simultaneously applied through the lumen.

15. The catheter of claim 14 comprising a plurality of apertures formed at spaced-apart locations about the outer surface of the catheter body, adjacent the distal end thereof.

16. The catheter of claim 15 comprising a plurality of medicament outlet apertures formed at spaced-apart locations about the outer surface of the distal tip member and oriented radially outward.

17. An ultrasound catheter for delivering ultrasonic energy and fluid concomitantly to a treatment location within a mammalian body, said catheter comprising:

an elongate flexible catheter body having a longitudinal axis, a proximal end, a distal end, an outer surface, and a first lumen extending longitudinally therethrough;

an ultrasound distal tip member disposed at the distal end of the catheter body;

a solid ultrasound transmission member extending longitudinally through said catheter body and being connected at the distal end thereof to the distal tip member, said ultrasound transmission member being coupleable to an ultrasound source such that ultrasonic vibration from said ultrasound source may be transmitted through said ultrasound transmission member to the ultrasonic distal tip member at the distal end of said catheter;

a fluid inlet formed near the proximal end of said catheter body for infusion of a fluid through a hollow lumen of said catheter; and a fluid outlet aperture formed in the distal tip of said catheter and oriented radially outward in relation to the longitudinal axis of the catheter body to permit the fluid to flow out of said catheter generally along the radial direction;

whereby a fluid may be infused through said catheter, and out of said outlet aperture concurrently with the delivery of ultrasonic energy to the distal end of the catheter.

18. The catheter of claim 17 wherein the medicament outlet aperture is formed in the distal tip member and oriented radially outward in relation to the tip and in fluid communication with the medicament inlet through the hollow lumen to permit medicament to flow out of said catheter.

19. The catheter of claim 18 further comprising a plurality of medicament outlet apertures disposed in spaced-apart locations about the outer surface of the catheter body adjacent the distal end thereof.

20. The catheter of claim 19 comprising a plurality of medicament outlet apertures disposed in the distal tip member at spaced-apart locations and oriented radially outward.

21. The catheter of claim 20 further comprising a guidewire lumen disposed in the catheter body separate from the first lumen so that the lumina are not in fluid communication with each other;

wherein fluid may be infused through the guidewire lumen and different fluid may be infused through the first lumen.

* * * * *

UNITED STATES PATENT AND TRADEMARK OFFICE
CERTIFICATE OF CORRECTION

PATENT NO. : 5,997,497
DATED : Dec.7, 1999
INVENTOR(S) : Henry Nita, Timothy Mills, Robert Siegel It is certified that error appears in the above-identified patent and that said Letters Patent is hereby corrected as shown below:

Title page, under "FOREIGN PATENT DOCUMENTS", change
"37077921A1    9/1987    Germany", to read
--3707921A1    3/1986    Germany--.

Column 4, lines 23, 32 and 34, change "22", to read --30--.

Column 4, line 40, change "24", to read --30--.

Column 4, line 59, change "50", to read --52--.

Column 5, lines 62 and 64, change "40", to read --30--.

Column 6, lines 4, 8, 9, 11, 17, 31, 35, 36, 54 and 56, change "40", to read --30--.

Column 8, line 19, change "30", to read --40--.

Column 8, lines 53 and 60, change "40", to read --30--.

Signed and Sealed this

First Day of August, 2000

Attest:

Q. TODD DICKINSON

*Attesting Officer*    *Director of Patents and Trademarks*